US011499903B2

(12) United States Patent
Hassell et al.

(10) Patent No.: US 11,499,903 B2
(45) Date of Patent: Nov. 15, 2022

(54) IN-SITU PROBE

(71) Applicant: Nirrin Technologies, Inc., Billerica, MA (US)

(72) Inventors: Bryan A. Hassell, Cambridge, MA (US); David P. Marchessault, Hopkinton, MA (US); Christopher R. Saulnier, Medford, MA (US); John C. Ho, Sudbury, MA (US); Walid A. Atia, Jamaica Plain, MA (US)

(73) Assignee: NIRRIN TECHNOLOGIES, INC., Billerica, MA (US)

( * ) Notice: Subject to any disclaimer, the term of this patent is extended or adjusted under 35 U.S.C. 154(b) by 0 days.

(21) Appl. No.: 17/030,032

(22) Filed: Sep. 23, 2020

(65) Prior Publication Data

US 2021/0088433 A1    Mar. 25, 2021

Related U.S. Application Data

(60) Provisional application No. 63/012,532, filed on Apr. 20, 2020, provisional application No. 62/904,560, filed on Sep. 23, 2019.

(51) Int. Cl.
*G01N 15/02* (2006.01)
*G01N 15/14* (2006.01)
*G01N 21/53* (2006.01)
*G01N 15/10* (2006.01)

(52) U.S. Cl.
CPC ......... *G01N 15/0205* (2013.01); *G01N 15/14* (2013.01); *G01N 21/53* (2013.01); *G01N 2015/1037* (2013.01)

(58) Field of Classification Search
CPC ................................................. G01N 21/8507
See application file for complete search history.

(56) References Cited

U.S. PATENT DOCUMENTS

| 5,373,160 | A | * | 12/1994 | Taylor | G01N 21/39 |
| | | | | | 250/338.5 |
| 5,483,080 | A | * | 1/1996 | Tam | G01N 21/51 |
| | | | | | 356/338 |
| 5,694,206 | A | * | 12/1997 | Curtiss | G01N 21/274 |
| | | | | | 356/414 |
| 5,836,883 | A | * | 11/1998 | Tsuchiya | G01N 21/49 |
| | | | | | 600/476 |

(Continued)

OTHER PUBLICATIONS

International Search Report and Written Opinion of the International Searching Authority, dated Nov. 27, 2020, from International Application No. PCT/US2020/052270, filed on Sep. 23, 2020. 22 pages.

(Continued)

*Primary Examiner* — Dominic J Bologna
*Assistant Examiner* — Jarreas C Underwood
(74) *Attorney, Agent, or Firm* — HoustonHogle LLP

(57) ABSTRACT

A device for monitoring a bioreactor is configured for in-situ analysis, e.g., by NIR, without the need for withdrawing a sample into a sample cell or into an ex-situ arrangement. The device can be inserted into a port of the bioreactor and provides a sample detection region defined by an optical element such as a lens and a photodetector. The electrical signal obtained from a photodetector that is part of the device can be directed to an analyzer via a detachable electrical connection.

17 Claims, 17 Drawing Sheets

(56) References Cited

U.S. PATENT DOCUMENTS

| | | | |
|---|---|---|---|
| 7,180,594 B2 | 2/2007 | Williams | |
| 7,319,522 B2 | 1/2008 | Havard et al. | |
| 7,508,521 B2* | 3/2009 | Liu | G01N 21/39 356/432 |
| 9,541,498 B1* | 1/2017 | Partridge, Jr. | G01N 21/3504 |
| 10,643,008 B2* | 5/2020 | Liu | G01N 21/39 |
| 2002/0158202 A1* | 10/2002 | Webber | F23N 5/003 431/75 |
| 2005/0264817 A1* | 12/2005 | Havard | G01N 21/532 356/442 |
| 2009/0059332 A1* | 3/2009 | DiFoggio | G01N 21/0303 356/73 |
| 2009/0185187 A1* | 7/2009 | Crist | G01N 21/8507 356/436 |
| 2012/0244608 A1 | 9/2012 | Selker et al. | |
| 2014/0036257 A1* | 2/2014 | Kramer | G01N 21/8507 356/128 |
| 2014/0287449 A1* | 9/2014 | Bonyuet | C12Q 1/02 435/29 |
| 2015/0247794 A1* | 9/2015 | Olesberg | C12Q 3/00 250/339.07 |
| 2019/0358632 A1 | 11/2019 | Hassell et al. | |
| 2021/0062133 A1 | 3/2021 | Hassell et al. | |

OTHER PUBLICATIONS

Cervera, A. E., et al., "Application of near-infrared spectroscopy for monitoring and control of cell culture and fermentation," Biotechnol. Prog., 25(6): 1561-1581 (2009).

Davies, A.M.C., "An Introduction to Near Infrared (NIR) Spectroscopy", http://www.impublications.com/content/introduction-near-infrared-nir-spectroscopy (2019).

Roggo, Y., et al., "A review of near infrared spectroscopy and chemometrics in pharmaceutical technologies," Journal of Pharmaceutical and Biomedical Analysis, 44 (3): 683-700 (2007).

International Preliminary Report on Patentability dated Apr. 7, 2022, from International Application No. PCT/US2020/052270, filed on Sep. 23, 2020. 17 pages.

* cited by examiner

IN-SITU PROBE

RELATED APPLICATIONS

This application claims the benefit under 35 USC 119(e) of U.S. Provisional Patent Application No. 62/904,560, filed on Sep. 23, 2019 and of U.S. Provisional Patent Application No. 63/012,532, filed on Apr. 20, 2020, both of which are incorporated herein by this reference in their entirety.

BACKGROUND OF THE INVENTION

Many processes in the chemical, biochemical, pharmaceutical, food, beverage and in other industries require some type of monitoring.

Sensors have been developed and are available to measure pH, dissolved oxygen (DO), temperature or pressure in-situ and in real-time. Common techniques for detecting chemical constituents include high performance liquid chromatography (HPLC), gas chromatography-mass spectroscopy (GCMS), or enzyme- and reagent-based electrochemical methods.

While considered accurate, many existing approaches for monitoring substances in a reactor are conducted off-line, tend to be destructive with respect to the sample, often require expensive consumables and/or take a long time to complete. In many cases, the equipment needed to perform these analyses is expensive, requires involved calibrations, and trained operators. Procedures may be time- and labor-intensive, often mitigated by decreasing the sampling frequency of a given process, thus reducing the data points. Often, samples are run in batches, after the process has been completed, yielding little or no feedback for adjusting conditions on an ongoing basis. Drawbacks such as these can persist even with automated sampling operations.

Various optical spectroscopy approaches are available to assess components, also referred to as analytes, in a sample. Among these, probably the most common is absorption spectroscopy. Incident light excites electrons of the analyte from a low energy ground state into a high energy, excited state, and the energy can be absorbed by both non-bonding n-electrons and π-electrons within a molecular orbital. Absorption spectroscopy can be performed in the ultraviolet, visible, and/or infrared region, with analytes of varying material phases and composition being interrogated by specific wavelengths or wavelength bands of light. The resulting transmitted light is then used to resolve the absorbed spectra, to determine the analyte's or sample's composition, temperature, pH and/or other intrinsic properties for applications ranging from medical diagnostics, pharmaceutical development, food and beverage quality control, to list a few.

Another option is Raman spectroscopy, which works by the detection of inelastic scattering of typically monochromatic light from a laser.

SUMMARY OF THE INVENTION

A need exists for robust, hands-free, non-destructive, real time techniques for identifying and/or quantifying constituents in a given process. Typically, the process is conducted in a vessel, e.g., a bioreactor. The contents of the bioreactor can change as the process unfolds and data obtained by the procedures and equipment described herein can be used to monitor, adjust and/or control process parameters.

In many of its aspects, the invention relates to a device and/or method for monitoring, in-situ, an ongoing process, such as, for example, a process conducted in a bioreactor. Cells and/or substances present in the bioreactor (or another vessel) are identified and often quantified using a suitable technique. In many implementations, the technique is near infrared (NIR) absorption spectrometry.

Some embodiments relate to an in-situ probe that can be inserted and/or maintained in a bioreactor and incorporates elements for interrogating as well as elements needed to analyze the contents of a bioreactor, e.g., in the NIR region of the electromagnetic spectrum. The analysis can be conducted in real time, in a nondestructive manner. Other embodiments relate to a system that includes a bioreactor monitored by an in-situ probe, in an automated manner, for example. Further embodiments relate to a method for performing an in-situ analysis using an in-situ probe.

In typical examples, the analysis is conducted without withdrawing a sample from the reactor. An interrogating beam of electromagnetic radiation is introduced into the reactor and traverses a pathlength formed within the reactor medium; transmitted radiation reaches a photodetector and generates an electrical signal that is conveyed and analyzed externally.

In general, according to one aspect, the invention features a device for monitoring a vessel. This device comprises an outer tube and a tip section at the end of the tube. The tip section has a sample detection region defined by an optical transmission port and an optical detection port, wherein light received through the optical detection port is detected by a photodetector housed in the tip section.

In examples, the device further comprises an inner tube housed in the outer tube for providing the light for the optical transmission port. This inner tube contains electrical wiring for the photodetector. In some examples, the inner tube contains optical fiber for carrying the light for the optical transmission port. In other examples, the inner tube defines a free space path for the light for the optical transmission port.

In many embodiments, a housing carried by the inner tube makes electrical connections to the optical detector.

A fitting on the outer tube is common for sealing with a port of a bioreactor.

Then, in operation, the light is generated by a tunable laser that sweeps a narrow band emission across an infrared spectral band.

In many cases, a focusing lens in the tip section is helpful for conditioning, i.e., focusing or collimating, the light transmitted across the sample detection region.

In general, according to another aspect, the invention features a method for monitoring a vessel. The method comprises inserting an outer tube with a tip section into the vessel, transmitting light across a sample detection region of the tip section from an optical transmission port to an optical detection port, and detecting the light received through the optical detection port with a photodetector housed in the tip section.

Often, the method further includes autoclaving the outer tube including the tip section prior to inserting the outer tube into the vessel.

Then, after inserting the outer tube into the vessel, an inner tube is inserted in some examples. This inner tube includes a housing into the outer tube.

In general, according to another aspect, the invention features a system comprising an in-situ probe inserted in a port of a reactor, wherein the probe includes a photodetector for receiving electromagnetic radiation that has propagated through a sample detection region defined by the photodetector and an optical element, and a controller for analyzing an electrical signal from the photodetector and including a laser generating the electromagnetic radiation.

In general, according to another aspect, the invention features a system comprising a bioreactor and a device for monitoring in-situ contents in the bioreactor. This device includes an outer tube inserted through a port of the bioreactor, a tip section at the end of the tube, the tip section having a sample detection region defined by an optical transmission port and an optical detection port, wherein light received through the optical detection port is detected by a photodetector housed in the tip section.

In general, according to another aspect, the invention features a method for monitoring a reactor. The method comprises directing a beam of electromagnetic radiation through a sample detection region within a reactor medium, wherein the sample detection region is defined by a lens and a photodetector, collecting an electrical signal from the photodetector, and analyzing the electrical signal to obtain a spectrum of a material in the sample detection region.

The in-situ probe, system and method present many advantages. Detachable parts that can be assembled and disassembled as needed offer flexibility and convenience. In many cases, the analysis process is simplified and accelerated. Moreover, the probe can include disposable parts and/or, importantly, components that can be autoclaved and reused.

Whereas many existing approaches rely on removing and/or circulating cells in loops external to the process vessel, typically through a pumping system, the equipment and procedures described herein reduce, minimize and often eliminate the exposure of the bioreactor contents to conditions external to the bioreactor. In addition, cells are prevented from being drawn into the pumping system.

Techniques such as the ones described herein also improve the quality of the analysis. For example, embodiments described herein can provide improved or even maximum signal to noise ratios. This is accomplished by launching a light beam straight out of a fiber and/or a free space link, through a sample gap, with the transmitted light impinging onto a photodetector. By having the detector cables running up the length of the probe, rather than using a return fiber optic cable leading to a photodiode, often external to the reactor, approaches described herein can rely on the signal to noise ratio (SNR) of the electrical cables, which generally are superior to fiber optics.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
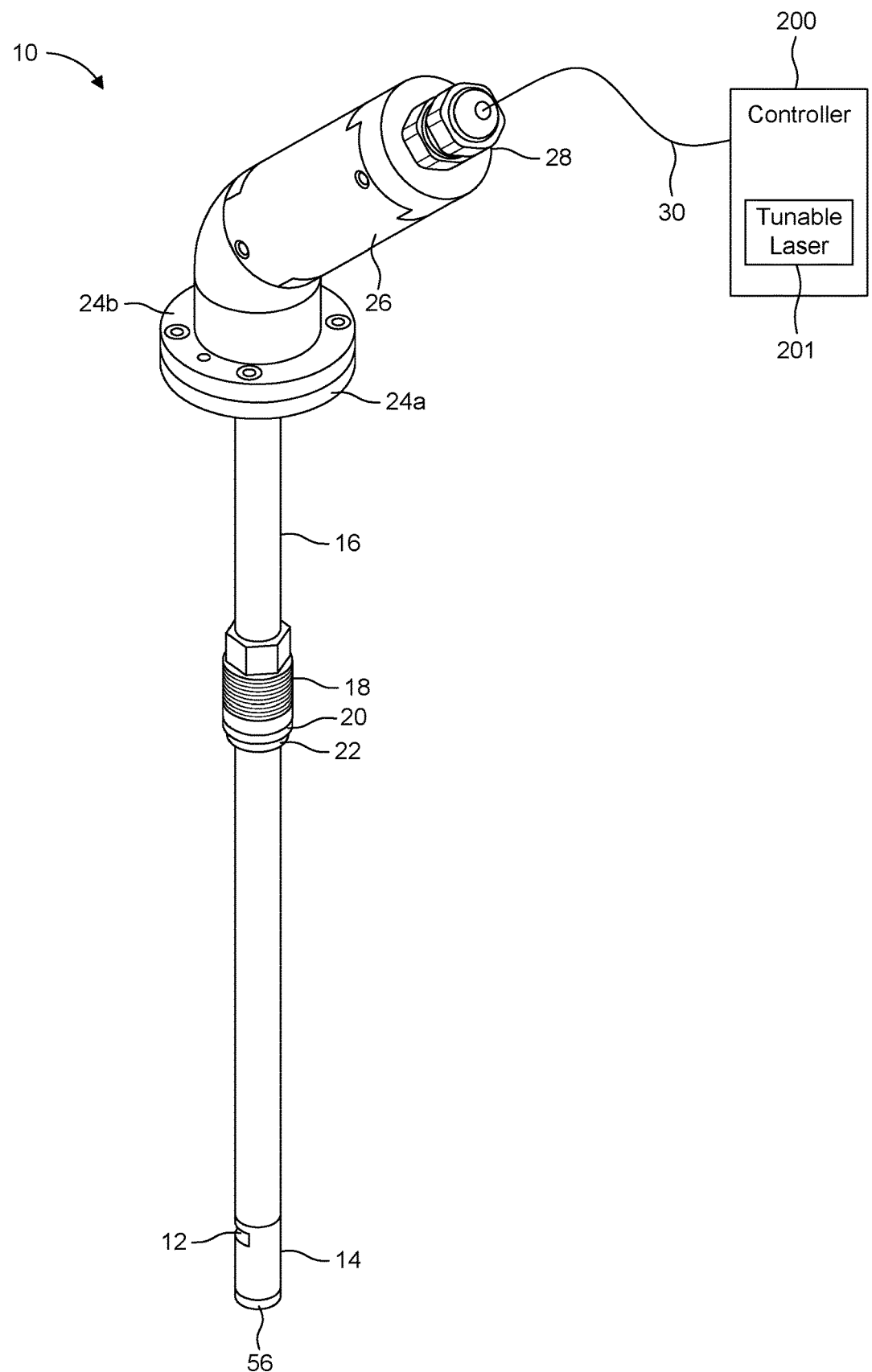
FIGS. 1 and 2 are, respectively, perspective and side views of one embodiment of an in-situ probe according to the invention.

The invention now will be described more fully hereinafter with reference to the accompanying drawings, in which illustrative embodiments of the invention are shown. This invention may, however; be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Many processes conducted in bioreactors require or benefit from a stringent of parameters such as pH, levels of oxygen, nutrients, metabolites and/or other species. In many of its aspects, the invention relates to a device and method for analyzing the contents of a bioreactor on an ongoing basis. Cells, for instance, and/or other reactor constituents can be detected, at various time intervals and the data can be used to assess conditions and, if necessary, adjust or optimize process parameters. Examples of processes that can be monitored include cell growth protocols, fermentations, and so forth. Bioreactors can feature a suitable design and can be characterized by a specific volume or dimensions, as known in the art or as developed in the future.

In one implementation, techniques described herein are practiced with a bioreactor that houses or is a cell culture system for the three-dimensional assembly, growth and differentiation of cells and tissues. The bioreactor can contain cells, culture media, nutrients, metabolites, enzymes, hormones, cytokines and so forth.

Analysis can utilize a spectroscopy system for determining the spectral response of the components in the sample cell in one or more of the following electromagnetic spectral regions: millimeter, microwave, terahertz, infrared (including near-, mid- and/or far-infrared), visible, ultraviolet (UV), x-rays and/or gamma rays. Further, the spectroscopy system can measure different characteristics, such as absorption spectra, emission (including blackbody or fluorescence) spectra, elastic scattering and reflection spectra, impedance (e.g., index of refraction) spectra, and/or inelastic scattering (e.g., Raman and Compton scattering) spectra, of analytes in the bioreactor.

Specific embodiments described herein rely on spectroscopy in the ultraviolet and visible regions, but mostly in the infrared region extending from 700 nanometers (nm) to 1 millimeter (mm) in wavelength and specifically including the near infrared (0.75-1.4 µm, NIR), short-wavelength infrared (1.4-3 µm, SWIR), mid-wavelength infrared (3-8 µm, MWIR), long-wavelength infrared (8-15 µm, MIR), and the far infrared (15-1000 µm, FIR) of the spectrum. Probing molecular overtone and combination vibrations, MR-SWIR spectroscopy covers the region of from 780 nanometer (nm) to 2500 nm of the electromagnetic spectrum. An overview of NIR spectroscopy can be found, for example, in an article by A. M. C. Davies in "An Introduction to Near Infrared (NIR) Spectroscopy", http://www.impublications.com/content/introduction-near-infrared-nir-spectroscopy, See also, Cervera, A. E., Petersen, N., Lantz, A. E., Larsen, A. & Gernaey, K. V. Application of near-infrared spectroscopy for monitoring and control of cell culture and fermentation, Biotechnol. Prog. 25, 1561-1581 (2009); and Roggo Y, et al., "A review of near infrared spectroscopy and chemometrics in pharmaceutical technologies", Journal of Pharmaceutical and Biomedical Analysis, Volume 44, Issue 3, 2007.

Among its strength, infrared spectroscopy presents a non-invasive, non-destructive investigative approach, typically involving fast scan times. A discussion of MR as applied to microfluidic and other systems is provided in U.S. patent application Ser. No. 16/419,690, to Hassell et al., filed on May 22, 2019 and incorporated herein in its entirety by this reference.

U.S. Provisional Patent Application No. 62/892,702, to Hassell et al, filed on Aug. 28, 2019 under the title Device and Bioreactor Monitoring System and Method and incorporated herein by this reference in its entirety, describes arrangements and techniques for obtaining samples to be analyzed, e.g., by NIR, using a sample tube that can be inserted into a vessel, e.g., a bioreactor or another type of vessel or arrangement used to conduct biochemical or chemical processes. The sample tube used for extracting a sample from the bioreactor can be combined or integrated with a sample cell configured for NIR interrogation and analysis.

According to embodiments described herein, measurements are taken within (inside) the reactor, typically without a need to withdraw a sample into a sample or flow cell or into an external (ex-situ) arrangement for taking a reading.

Many implementations of the present invention employ an outer tube of stainless steel which is sealed by a photodetector, such as a photodiode in a windowed package, and an optical component, in many cases a focusing lens. These two elements define an optical transmission port and an optical detection port on either side of a sample detection region. Being in contact with the fluid inside the bioreactor, their spacing can be the pathlength of the laser light.

In other embodiments, the photodetector and the optical component are behind respective windows for ease of cleaning, however.

In practice, the outer tube is placed into a bioreactor and then another stainless steel cap with O-ring can be attached on top to create a seal.

This entire assembly can be autoclaved.

After autoclaving, the cap is removed. An inner tube, containing, for example, the fiber optic collimator, which guides the beam downward into the focusing lens, as well as a connector, e.g., a 3-pin POGO connector, which connects to the other connectors from the photodetector can be inserted into the outer tube. Some designs do not employ a collimator and use the inner tube to form a free space path to propagate the beam of electromagnetic radiation towards the focusing lens.

One embodiment of an in-situ probe according to aspects of the invention is described with reference to FIGS. 1-6.

Figure 2:
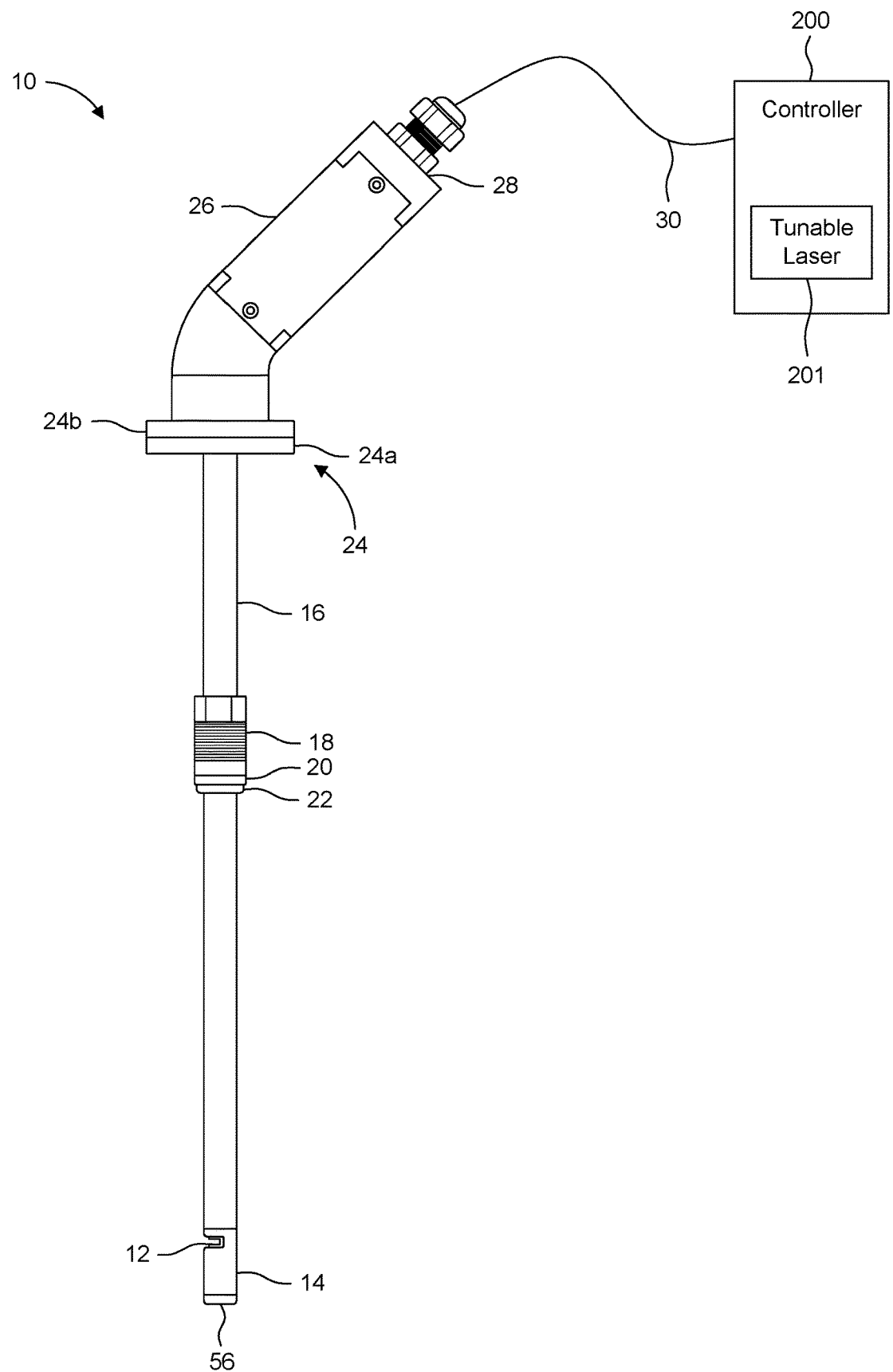
Figure 3:
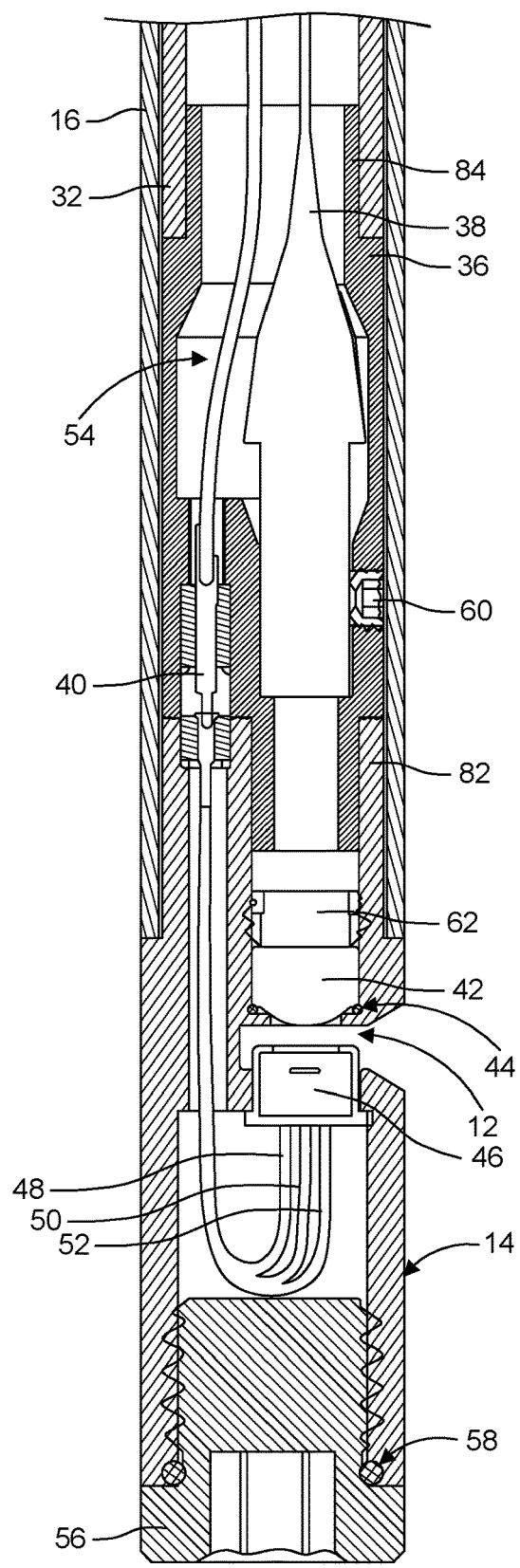
FIG. 3 is a cross-sectional view of the tip section of the in-situ probe of FIGS. 1 and 2 according to one embodiment.

Shown in FIGS. 1 and 2 is in-situ probe 10, configured for placing and/or maintaining a sample detection region 12 within the bioreactor. FIG. 3 is a longitudinal cross-sectional view of a tip section 14 of the in-situ probe.

As seen in these figures, the sample detection region 12 is located at a tip section 14 of probe 10 and can be shaped with an indentation formed, as further described below. The sample detection area is defined by an optical transmission port and an optical detection port. In this embodiment, the optical transmission port is a focusing lens (or another suitable optical component) or a window optically after the focusing lens. The optical detection port is a photodetector, or a window before the photodetector, facing the lens across the detection region 12. Tip section 14 further includes a proximal necked-down portion 82 that is inserted into the distal end of an outer tube 16, e.g., a 12-mm diameter stainless steel tube. The outer surface of the necked-down portion 82 is bonded to the inner surface of the distal end of the outer tube 16. The outer tube 16 is configured to receive an inner tube 32.

Since many bioreactor headplates are equipped with ports for receiving various fittings which can be screwed in, fitting 18, optional Teflon washer 20 and EPDM rubber O-ring 22, or another suitable arrangement, provide a seal on the headplate at the top a bioreactor. In more detail, fitting 18 can be a PG13.5 18 fitting having the standard thread typically used on bioreactor headplates. Optional Teflon washer 20 (which does not provide a seal) can be used as a spacer to ensure sealing on certain bioreactor headplates that may have a deeper threaded section for the PG13.5 fitting. The EPDM O-ring 22 creates the seal between the headplate and the bottom of the Teflon washer 22 as the Pt 313.5 fitting 18 is tightened.

The dimensions of tip section 14 and the outer tube 16 can be selected according to the size of the reactor. In many situations, the longitudinal distance between the fitting 18 and the optical detection region 12 of the tip section 14 is configured to expose detection area 12 to the reactor medium being monitored and specifically a portion of that medium that is representative of all of the medium in the bioreactor, rather than possibly unmixed medium along a wall of the reactor. In one illustrative example, the distance between the fitting 18 and the optical detection region 12 is at least 1 centimeter (cm), e.g., at least 2, 3, 4, 5, 10, 15, 20, 25, 30, 35, 40, 45, 50, 55, 60, 65, 70, 75, 80, 85, 90, 95 or 100 cm. Tip section 14 can be smaller, for miniaturized reactor designs, for instance, or larger, for some industrial scale applications.

Flange arrangement 24 can be made (entirely or in part) of stainless steel and includes upper flange 24b, for joining electronic housing 26 to bottom flange 24a. The lower end of tip section 14 is capped by plug 56, made, for instance, of stainless steel. Rubber (EPDM) O-ring 58 provides a leak-tight seal.

Within the distal end of the inner tube 32 is a proximal end 84 of a housing 36. The housing 36 includes elements such as collimator 38 and an electrical connections, e.g., 3-pin POGO connector 40. For analysis, a light beam (generated by a laser 201 in the controller 200) is directed through collimator 38 and focused by lens 42, the latter being seated onto a rubber (EPDM) O-ring 44. From lens 42, typically a molded aspheric lens, light propagates through the bioreactor medium present in sample detection region 12 and reaches the packaged photodiode 46, provided, respectively, with anode, cathode and ground wires 48, 50 and 52. These wires serve to transmit signal from the photodiode to a female connector of the tip section 14 to the male connector 40 of the housing 36; from there, the signal follows along wires 54, through tube 32, electronics housing 26, cable gland 28 and wire harness 30, for signal analysis, e.g., by controller 200. In general, during operation, the light from the tunable laser 201 is coupled into the wire harness 30 and specifically optical fiber 124 and travels through the inner tube 32 of be probe. The light exiting from the fiber is conditioned and collimated by the collimator 38 and focused by aspheric lens 42 to propagate through the sample detection region. The transmitted light is then detected by the photodiode 46 after being modulated by the sample in the area 12, which will tend to preferentially absorb some wavelengths relative to others.

The length or the wires and/or optical fiber employed can be configured according to the overall size of the probe, which, in turn, can depend on factors such as the size of the reactor being monitored.

The controller 200 monitors the response of the photodiode 46 via the anode wire 48, cathode wire 50, and ground wire 52. The detachable electrical connections are made through the 3-pin connector 40. Thus, the controller can resolve the absorption spectra of the sample by monitoring the spectral scanning of the tunable laser over its scan band relative to the time-response of the photodiode 46. Generally, the tunable laser or tunable laser system sweeps its narrow band emission over some region of the electromagnetic spectrum such as the NIR and/or SWIR regions, or portions thereof.

It is possible to convey the transmitted light, e.g., via fiber optics, to a photodetector external to the reactor. However, an arrangement in which the detector (photodiode 46 in FIG. 3) is part of the in-situ probe exploits signal to noise ratio (SNR) advantages of transmitting electrical signals, e.g., along wires 48, 50, 52 and 54 (relative to directing light transmitted through the sample detection region 12 to an external photodiode detector, via fiber optics).

Stainless steel set screw 60 secures the collimator 38, while a hollow stainless steel set screw 62 can be employed to apply force to the back of the molded aspheric lens 42 and create a seal with EPDM O-ring 44 and the stainless steel tip body.

Figure 4A:
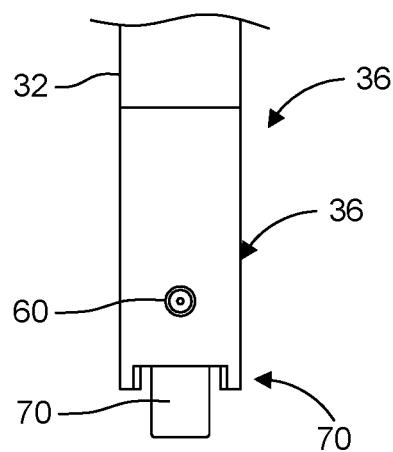
FIGS. 4A and 4B are views of the alignment elements used in assembling the in-situ probe of FIG. 1.
Figure 4A:
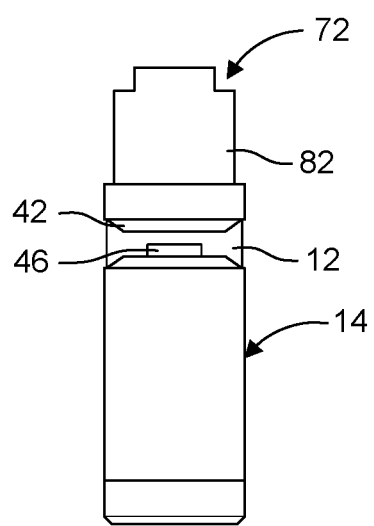
Figure 4B:
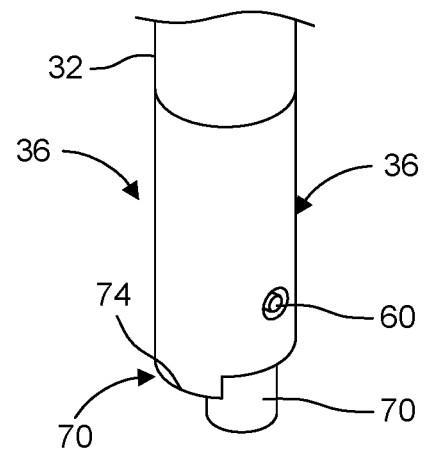
Figure 4B:
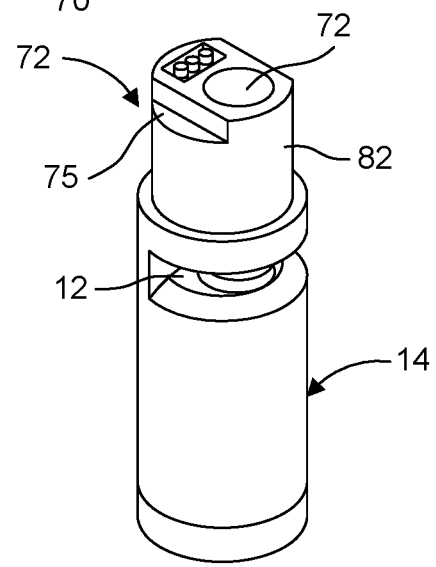

FIGS. 4A and 4B are views of an arrangement suitable for the assembly of the housing 36 (including, as already described, collimator 38 and the 3-pin POGO connector 40) and the lower tip section 14. The lower tip section 14 includes sample detection region 12, defined by lens 42 and photodiode 46. The lower tip section 14 is a housing that can be fabricated from molded or additively manufactured plastic or other resin or machined from metal.

For ease of assembly, housing 36 and tip section 14 are provided, respectively, with male alignment features 70 and female alignment features 72 along with shoulders 74 and grooves 75.

Figure 5A:
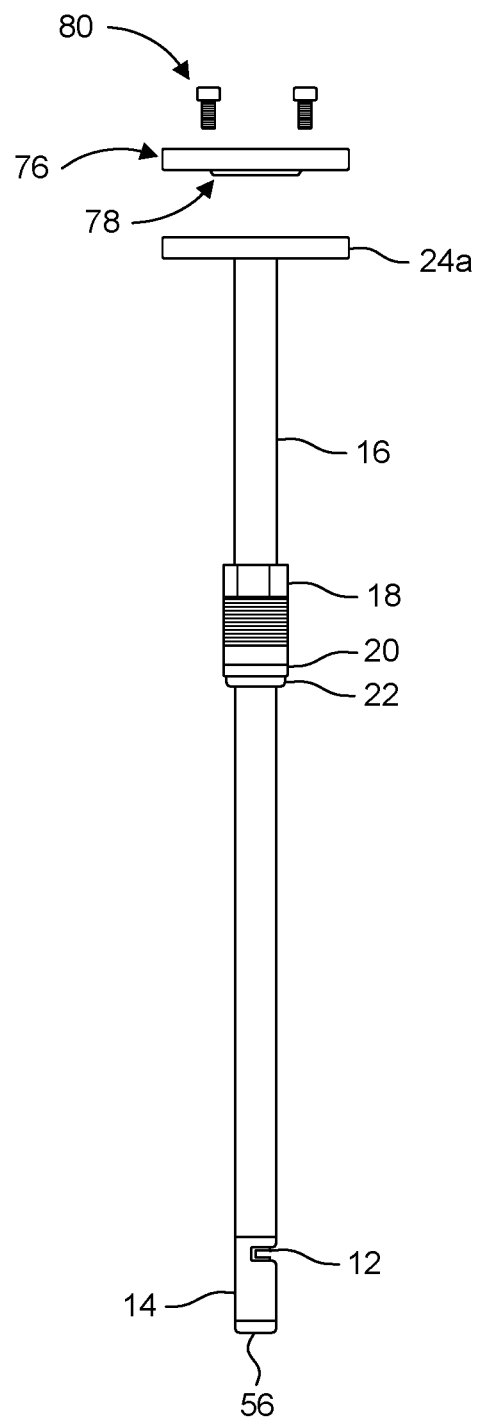
FIGS. 5A and 5B are diagrams illustrating the assembly of an autoclavable component of the in-situ probe of FIG. 1.
Figure 5B:
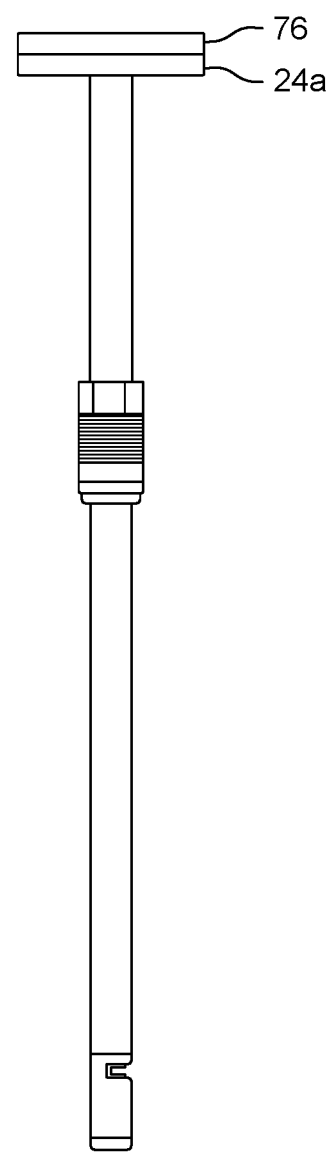

A probe such as described above can involve detachable parts, facilitating autoclave treatment of a portion of the in-situ probe from which optical fiber and electrical wire connections have been removed. For example, shown in FIGS. 5A and 5B is an autoclavable arrangement in which electronics housing 26 and the inner tube 32 of the in-situ probe 10 (see FIGS. 1 and 2) is withdrawn from the outer tube 16 and is replaced with a stainless steel cap 76 sealing the proximal end of the outer tube 16. In more detail, flange 24a of flange arrangement 24 (FIGS. 1 and 2) is covered which stainless steel cap 76, using EPDM rubber O-ring 78 and screws 80.

Figure 6:
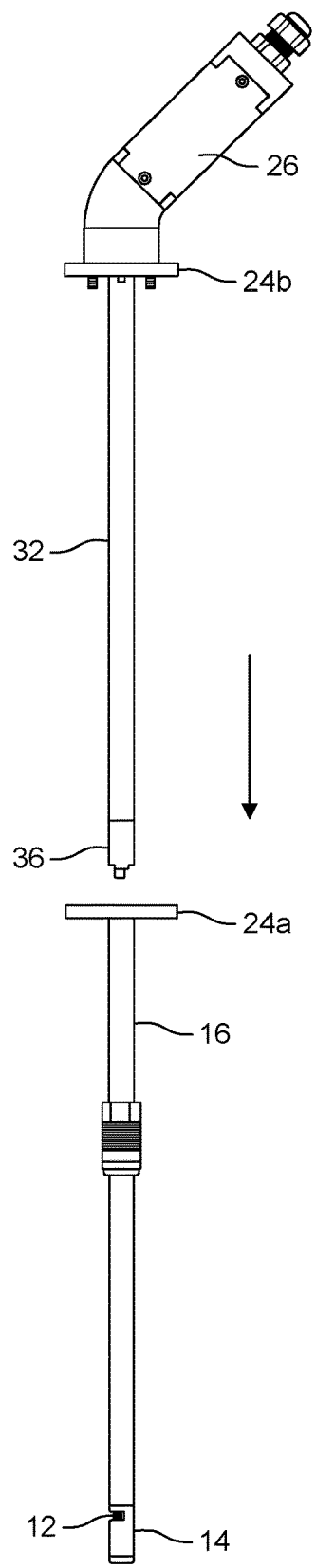
FIG. 6 is a diagram illustrating the assembly of the outer and inner tubes to produce the in-situ probe of FIG. 1.

Once autoclaving is completed, the outer tube 16 and the tip section 14 are inserted into the sterile or otherwise controlled environment inside the bioreactor. Then during operation, the stainless steel cap 76 can be removed and the in-situ probe 10 can be assembled as illustrated in FIG. 6. Specifically, inner tube 32 with the housing 36 is inserted into outer tube 16 and flange 24b is attached to flange 24a, thus bringing together electronics housing 26 and the various components described with reference to FIG. 3. The housing 36 mates with the tip section 14 and the male electrical connector 40 of the housing 36 connects to the female electrical connector of the tip section 14.

Figure 7:
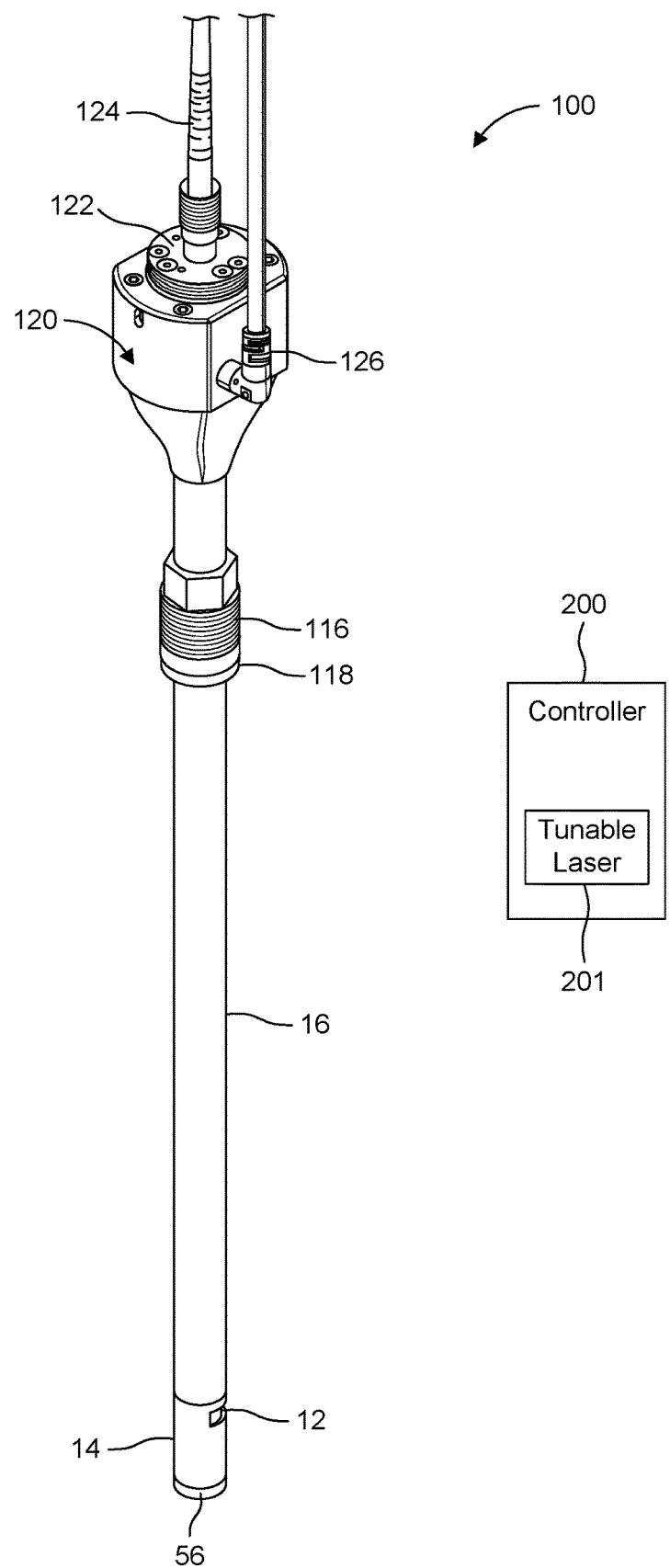
FIGS. 7 and 8 are, respectively, isometric and side views of another embodiment of an in-situ probe according to the invention.
Figure 8:
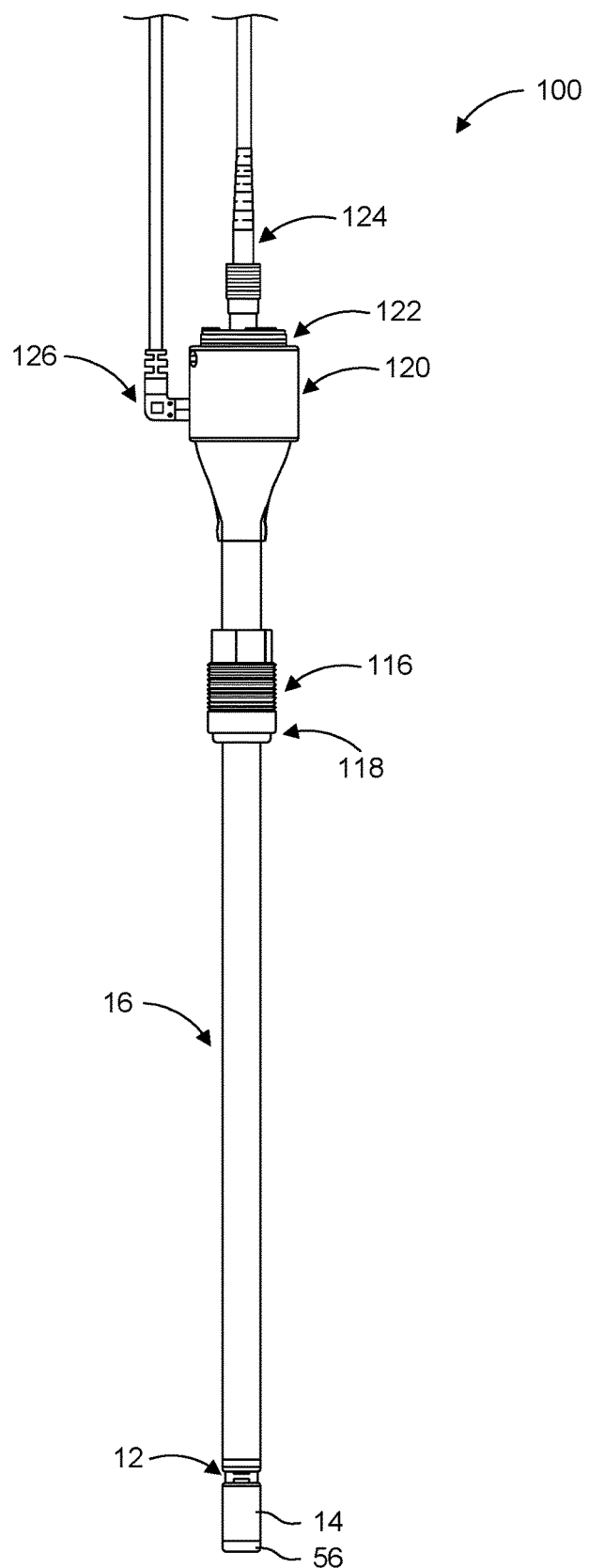

Other embodiments of an in-situ probe can be employed. FIGS. 7 and 8, for example, are views of in-situ probe 100, configured for deploying a sample detection region 12 within the bioreactor and conducting an in-situ analysis of the reactor contents, using, e.g., MR spectrometry.

As seen in these figures, in-situ probe 100 includes a tip section 14, comprising an outer tube 16, made, for instance, from a 12 mm stainless steel tubing, and fiber port housing 120, provided with fiber optical port adjuster 122, for receiving optical fiber 124. Signal cable and connector 126, can be attached to or detached from the fiber port housing, as further described below.

Adjustable PG 13.5 fitting 116 and O-ring 118 can be used to create a seal at an existing port of a bioreactor headplate, as described above with reference to elements 18 and 22 in FIGS. 1 and 2. Since the embodiment illustrated in FIGS. 7 and 8 does not require a spacer, no Teflon washer (such as optional Teflon washer 20 in FIGS. 1 and 2) is needed to fit the probe at the reactor headplate.

Below sample detection region 12, probe 100 terminates with plug 56 (made of stainless steel, for example).

Figure 9:
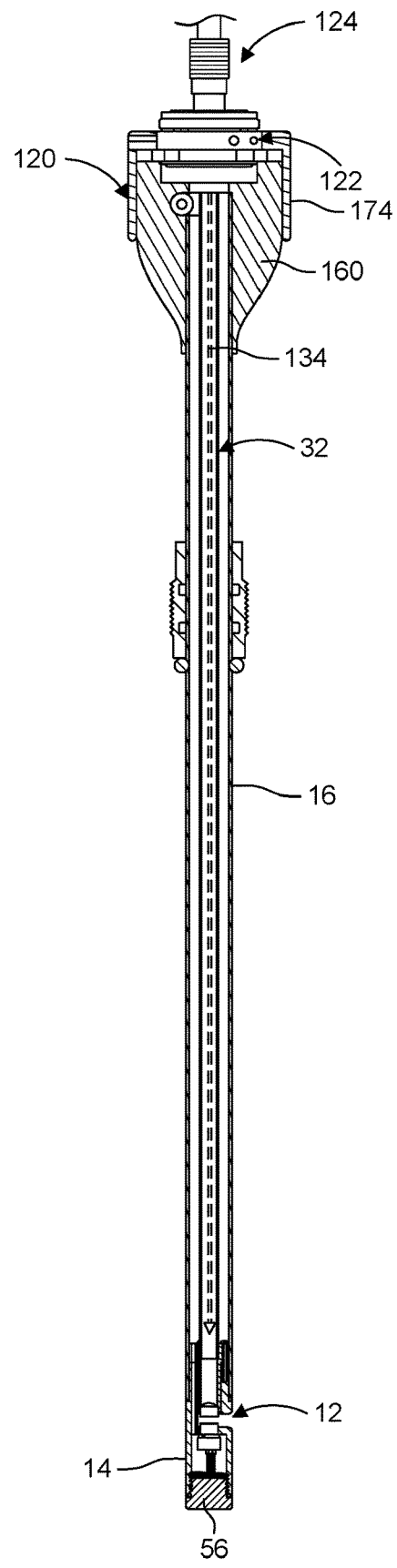
FIG. 9 is a cross-sectional view of the in-situ probe of FIGS. 7 and 8.

FIG. 9 is another embodiment of the probe 100. It includes inner tube 32, for optical beam isolation. The inner tube 32 defines an optical beam free space path 134 along the centerline of the inner tube 32 for propagating an electromagnetic energy beam, thus avoiding the need for optical fiber in the probe. The beam (generated, e.g., by the tunable laser or another suitable source, not shown in FIG. 9) is brought into inner tube 32 of the in-situ probe via upper section 174 of fiber port housing 120. Designed to be detachable, upper section 174 fits over a lower section 160, connected to the outer tube 16.

Figure 10:
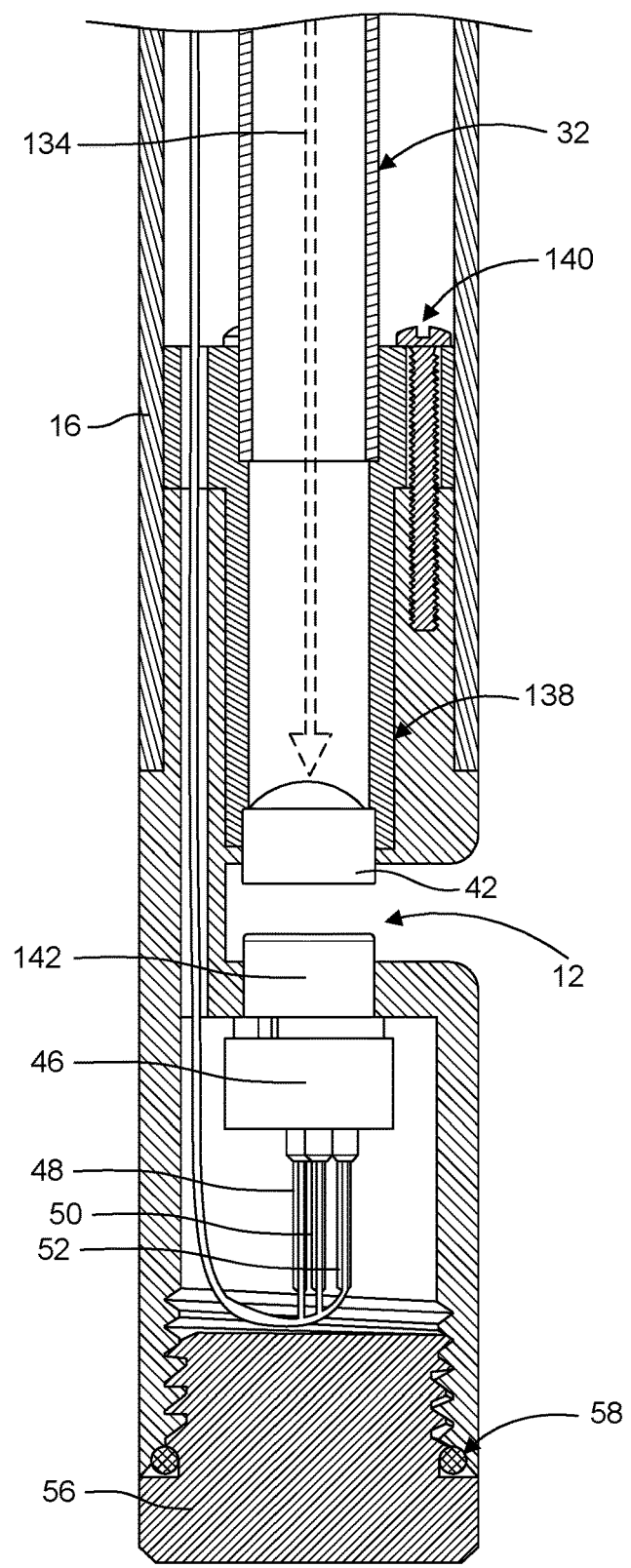
FIG. 10 is a cross-sectional of the tip section of the in-situ probe of FIGS. 1 and 2.

For analysis, electromagnetic radiation, e.g., in the NIR frequency region, is transmitted along the free space optical beam path 134, in the direction of the arrow, as illustrated in FIG. 10, The beam is focused by aspheric lens 42, supported by lens mount 138. The latter is secured with lens mount screw 140, made, e.g., of stainless steel.

After having passed through sample detection region 12, the transmitted light reaches photodiode 46. In this example, the photodiode 46 is located behind a window 142 that defines the distal extent of the sample detection region 12. The photodiode 46 provides a three-pin photodiode connector for photodiode anode wire 48, photodiode cathode wire 50, and photodiode ground wire 52. The photodiode connector and wires are protected in leak-tight fashion by fitting plug 56 and rubber (e.g., EPDM) O-ring 58. Signal exits the in-situ probe via signal cable and connector 126 and is directed to an analyzer, e.g., to controller 200 (FIGS. 1 and 2) or component thereof, for processing.

The length of the wires and/or optical fiber employed can be configured according to the overall size of the probe, which, in turn, can depend on factors such as the size of the reactor being monitored.

Relative to an alternative arrangement in which light that has passed through the sample detection region 12 is transmitted, via fiber optics, e.g., to an external photodiode detector, an arrangement which includes the detector (photodiode 46 in FIG. 3) as part of the in-situ probe and thus transmits an electrical signal (e.g., to controller 200) can lead to improvements in the SNR.

Probe 100 can involve detachable parts, facilitating autoclave treatment of a section of the probe from which the connection to fiber optics and to electrical wires has been removed.

Figure 11A:
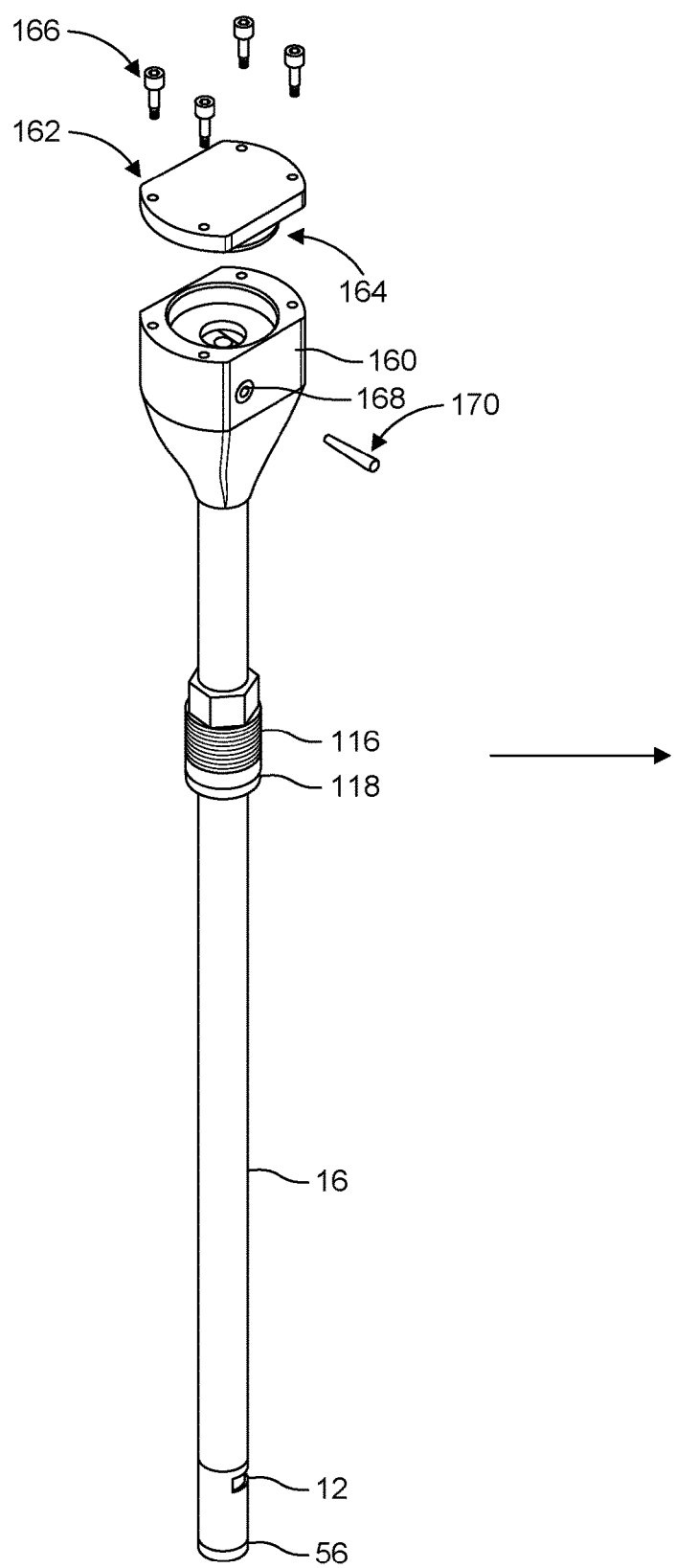
FIGS. 11A and 11B are diagrams illustrating the preparation of an autoclavable component of the in-situ probe of FIGS. 7 and 8.
Figure 11B:
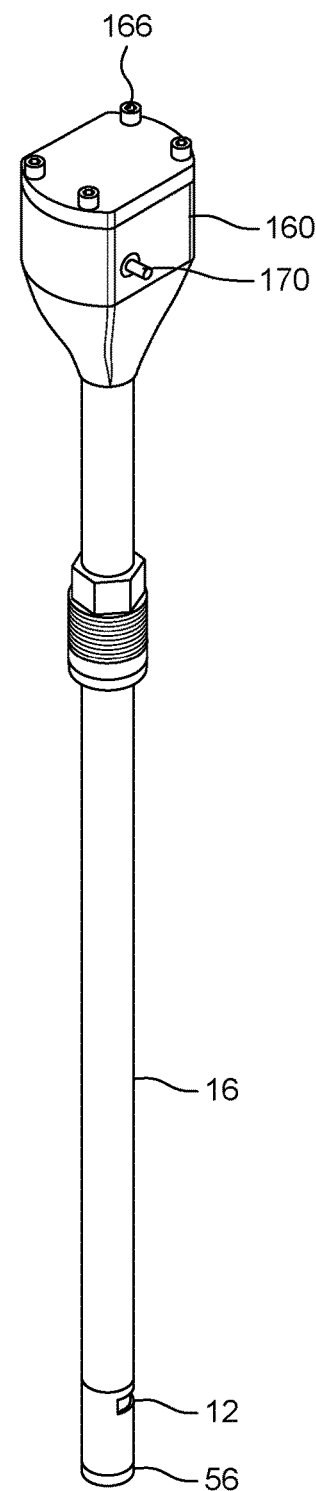

Preparing the autoclavable portion of in-situ probe 100 for autoclaving is illustrated with reference to FIGS. 11A and 11B. As seen in these figures, the autoclavable portion of in-situ probe 100 does not include components such as section 174 of fiber port housing 120 (see, e.g., FIGS. 7 and 8). Rather, section 160 of optical port housing 120 (FIGS. 1-3) is covered by stainless steel cap 162, which is supported on a rubber (e.g., EPDM) O-ring 164. The cap 162 can be secured using stainless steel screws 166. Also absent is signal cable and connector 126 (FIGS. 1 and 2), opening 168 being closed using, for instance EPDM rubber plug 170.

After the autoclave treatment is completed, cap 162 and plug 170 can be removed.

Figure 12:
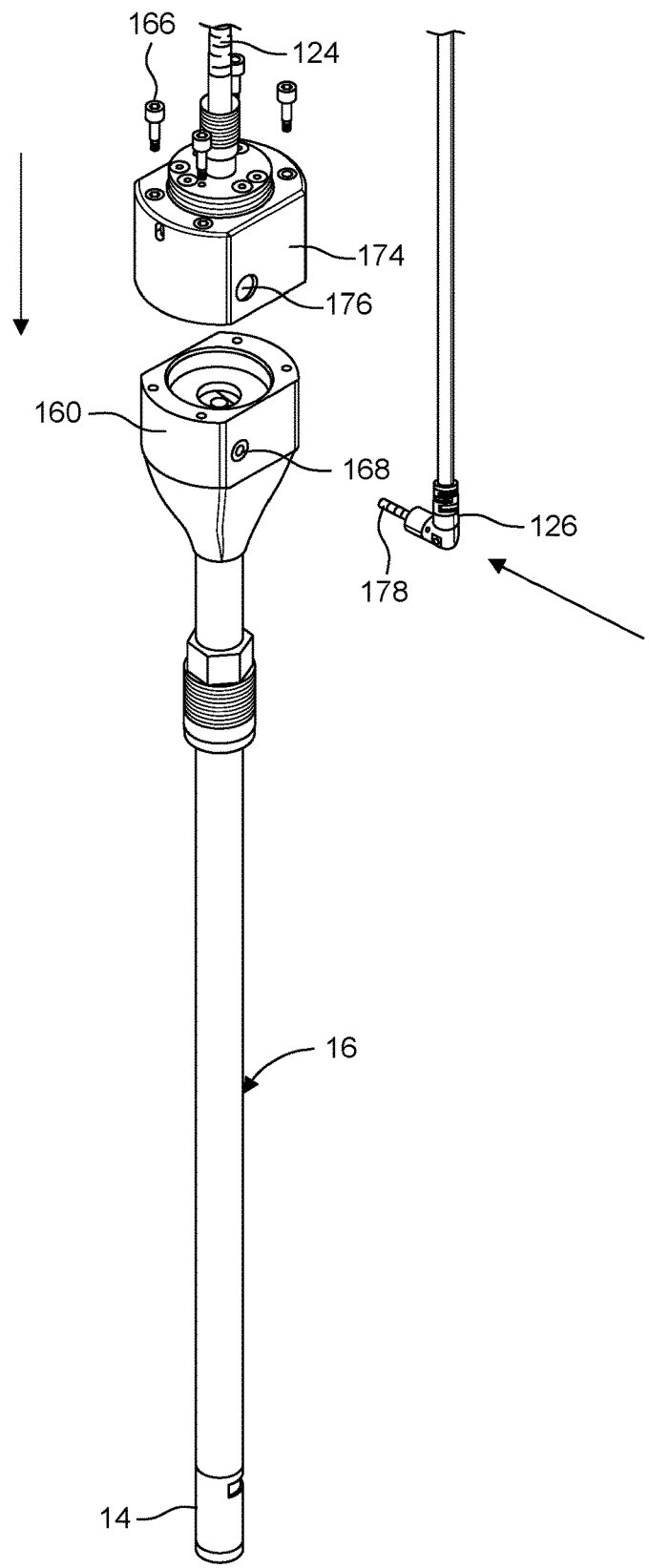
FIG. 12 is a diagram illustrating the assembly of the in-situ probe of FIGS. 7 and 8.

The assembly of the in-situ probe 100, in preparation for use, is illustrated in FIG. 12. It involves placing section 174 of optical port housing 120, over section 160, in the direction of the downward arrow, aligning opening 176 with hole 168, which is threaded to receive end 178 of signal cable and connector 126.

The in-situ probe can be employed to monitor and/or control a bioreactor automatically, using a suitable arrangement or system. In some embodiments this arrangement or system includes a controller, e.g., controller 200 in FIGS. 1, 2, 7 and 8). Part of controller 200 is a narrow band tunable light source 201 such as a tunable laser to interrogate specific wavelengths or wavelength bands of the electromagnetic spectrum to perform absorption spectroscopy on the contents of a reactor. The controller 200 also includes a single board computer, in one example, for monitoring the response of the photodiode 46 as a function of the instantaneous wavelength of the tunable laser in order to resolve the absorption spectrum of the material in the sample detection region 12.

In operation, the laser source 201 spectrally sweeps through a portion of the wavelength band such as from 780 nanometer (nm) to 2500 nm of the electromagnetic spectrum, or a portion thereof. This light is supplied to the probe via the wire harness 30 (FIGS. 1 and 2) or optical fiber 124 (FIGS. 7 and 8) and is directed through the center of the stainless steel inner tube 32 (see, for example, FIGS. 2 and 8) either in a fiber or a free space beam. Optical elements such as a collimator, lens, etc. are used to form and propagate a beam across the sample detection region 12. Light that has passed through the sample detection region is detected by photodiode 46.

Desired scanning parameters can be set and scanning can be conducted according to a suitable scanning program. In one example, the frequency of measurement is set to about every 5 minutes. In many implementations, the sampling is repeated with any desired frequency over any desired time period. For example, sampling is repeated (e.g., at a few minute-intervals) to monitor the entire reactor process (e.g., for a week, two weeks, three weeks or longer).

Further aspects of the invention relate to a system in which a reactor is monitored and/or controlled using an in-situ probe such as described above.

Figure 13:
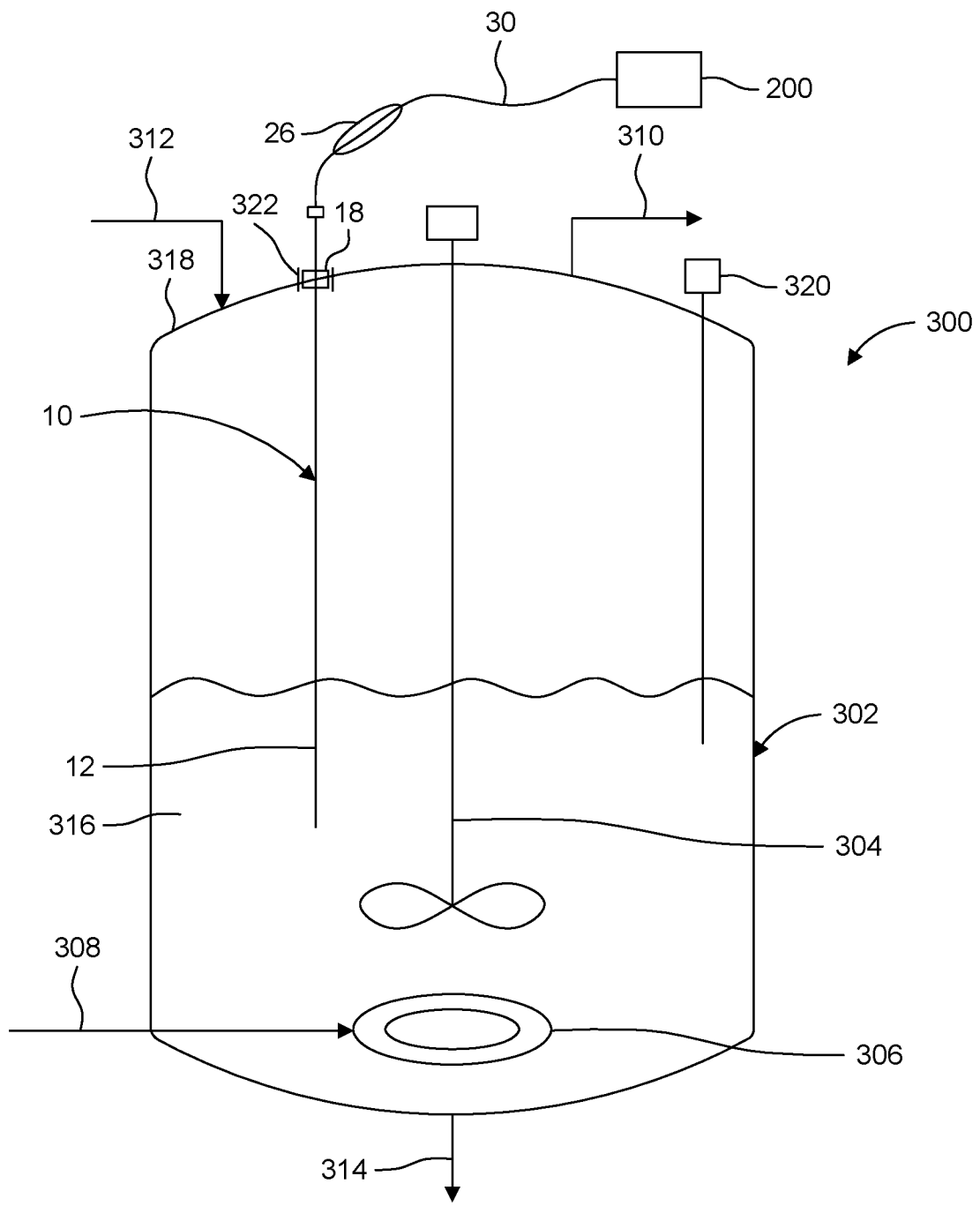
FIG. 13 is a diagram of a system in which a stirred tank reactor is provided with an in-situ probe according to embodiments of the invention.

Any number of reactor types can be employed. For example, shown in FIG. 13 is system 300 including a bioreactor 302, monitored by an in-situ probe such as, for instance, probe 10 in FIGS. 1-2 or probe 100 in FIGS. 7-8, and controlled by a controller 200. For illustrative purposes, the reactor 302 in FIG. 13 is a stirred tank reactor, which can be a continuous, semi-continuous or batch type. Stirred tank reactor 302 is provided with a motorized impeller 304 and sparger 306. Air is supplied to the sparger via conduit 308, while gas exits the reactor through conduit 310. Conduit 312 is used to supply ingredients to the reactor, while product can be collected via conduit 314.

Culture medium 316 is monitored by in-situ probe 10, which is provided with sample detection region 12 (FIGS. 1 through 3) and is secured to a port 322 in the bioreactor headplate 318 using fitting 18 (FIGS. 1 and 2). In operation, a light beam generated by the laser in the controller 200 and electrical signal from the photodiode 46 are transmitted to and from the probe via wire harness 30. Other process parameters (pH, oxygen levels, etc.) can be monitored using one or more probes 320 which also can be controlled by controller 200 or independently of controller 200.

Figure 14:
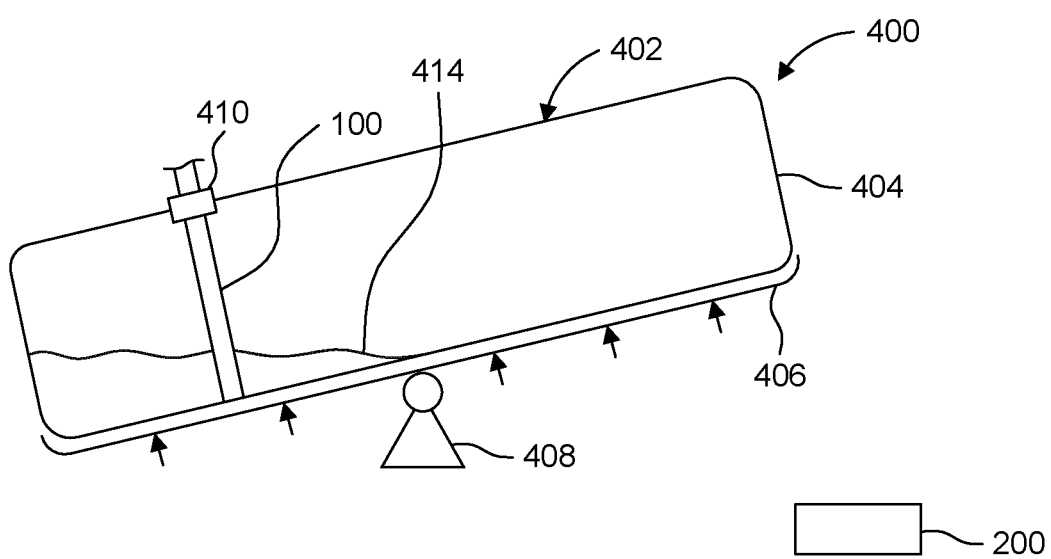
FIG. 14 is a diagram of a rocking bioreactor monitored by an in-situ probe controlled by a controller.

Shown in FIG. 14 is a diagram of a system 400 in which an in-situ probe such as probe 10 (FIGS. 1-2) or probe 100 (FIGS. 7-8), for instance, is inserted to monitor and/or control a rocking bioreactor 402, which includes bag 404, supported on a heated plate 406. A typically gentle rocking motion is generated by motorized base 408. The in-situ probe (e.g., probe 100 in FIGS. 7 and 8) is inserted via top port 410. Analysis of the bag contents 414, can be performed using controller 200, essentially as described above.

Figure 15:
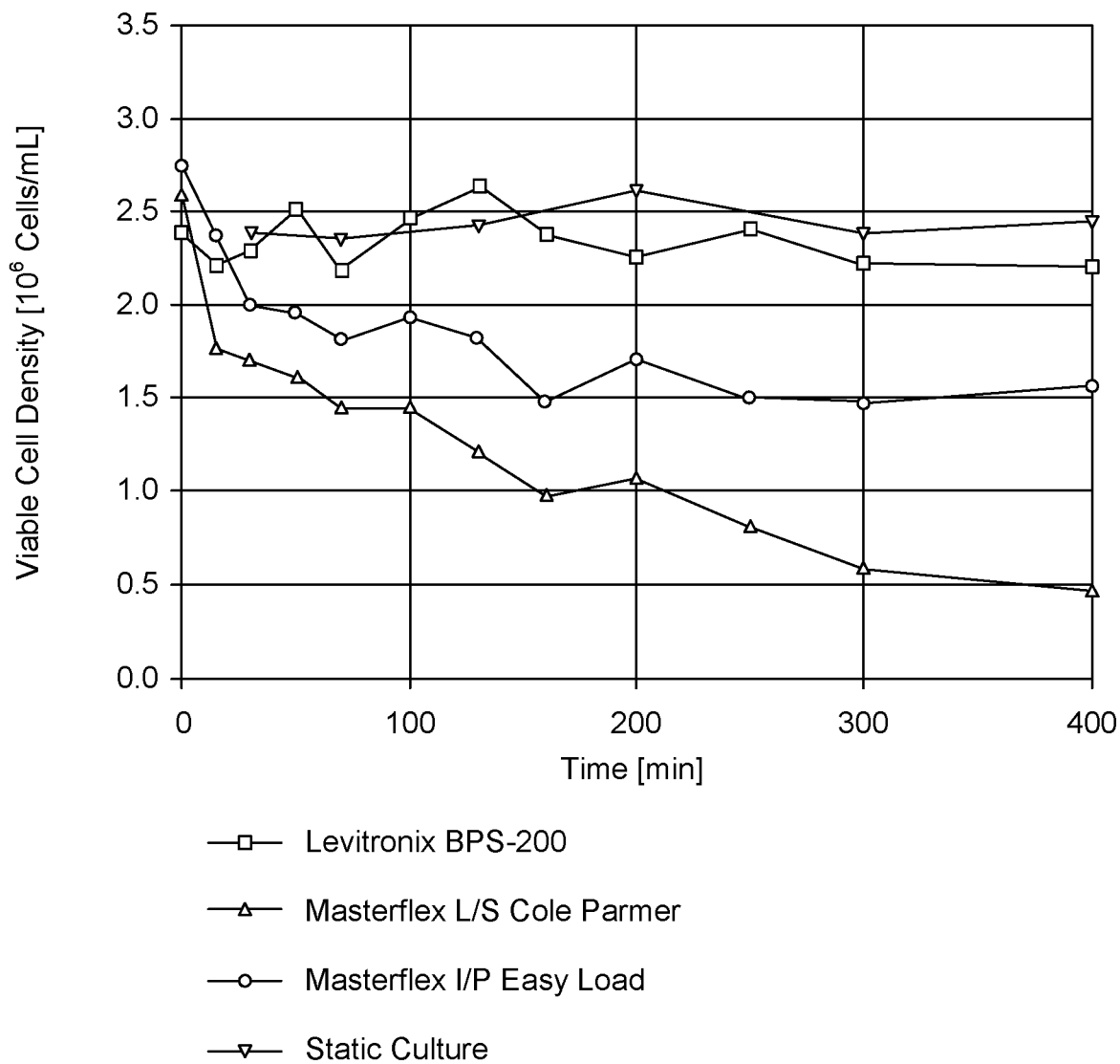
FIG. 15 is a series of plots showing viable cell densities under various sampling and analysis conditions.

Advantages associated with arrangements that reduce, minimize or prevent cell handling (drawing the cells through the pumping system, for example) are illustrated in FIG. 15. The data show the impact of various techniques on viable cell densities. A levitating pump, for example, does not involve much cell touching and yields good cell viability. For cells that are not drawn and circulated in the pumping system, as described herein, results are expected to look very similar to those obtained with the static culture.

Figure 16:
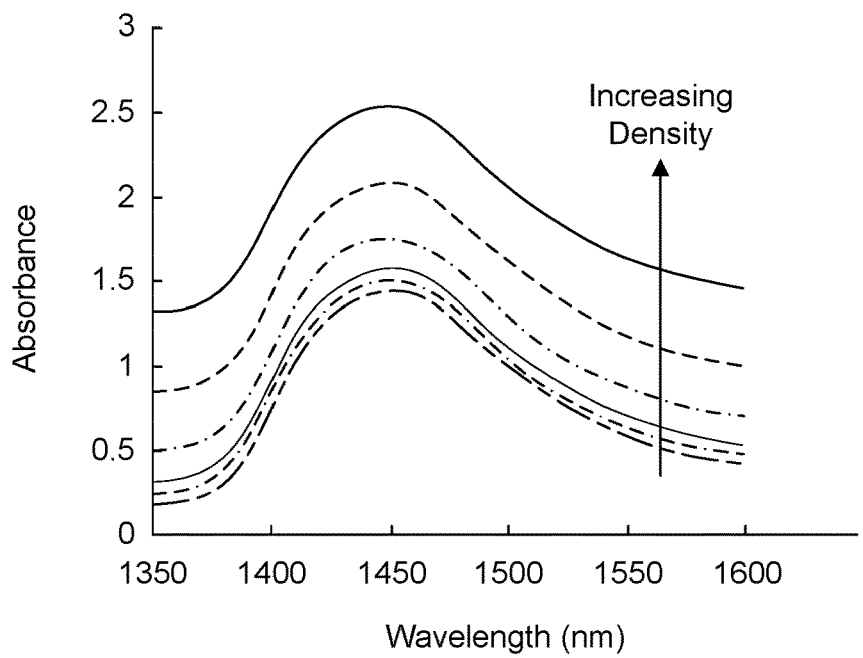
FIG. 16 shows plots in which samples of increasing cell densities are scanned in the NIR wavelengths, leading to increased scatter of the beam and thus an apparent increased absorbance.

The in-situ probe described above can be applied in various situations. In one example, the process parameter monitored is cell growth. Shown in FIG. 16, for example, are scans of samples of increasing cell densities in the NIR wavelengths, leading to increased scatter of the beam and thus an apparent increased absorbance.

Figure 17:
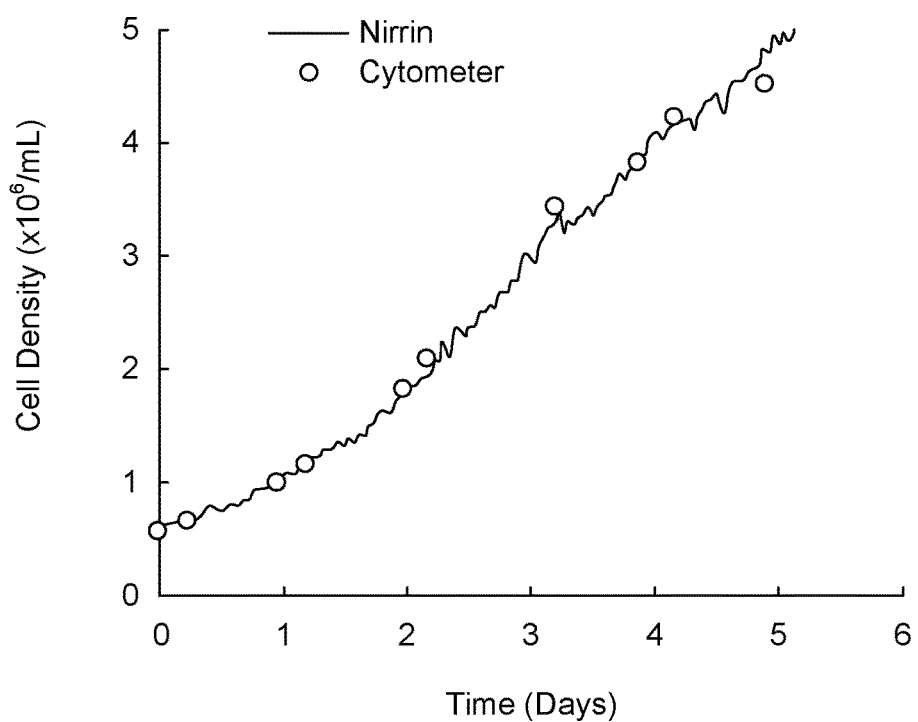
FIG. 17 shows a comparison of cell density versus time measured by cytometry and NIR spectrometry.

FIG. 17 compares the in-situ monitoring of CHO cells grown in a bioreactor. From spiking cells and then counting off-line, it is possible to build a calibration model, which then may be used to monitor the growth of cells in a more complex bioreactor.

Figure 18:
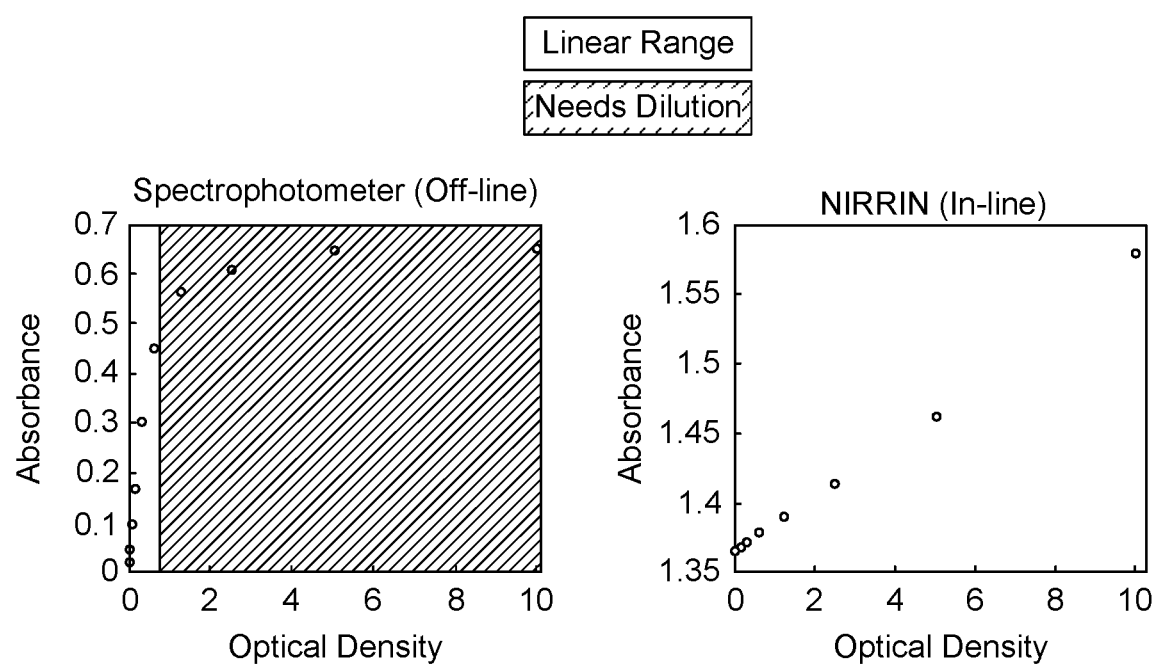
FIG. 18 presents a comparison of samples of *Pichia* growing in a shake flask. NIR measurements were performed with an in-line probe taking samples automatically and reading absorbance at approximately 1450 nm and comparing to off-line measurements from a standard spectrophotometer.

FIG. 18 compares samples of *Pichia* growing in a shake flask. NIRRIN measurements were performed with an in-line probe taking samples automatically and reading absorbance at approximately 1450 nm and were compared to off-line measurements from a standard spectrophotometer.

In one example, embodiments of the invention are applied to the field of cell and gene therapy. Typically, such treatments involve collecting cells from a subject's body, modifying (or reprogramming) the cells and growth of these cells to a number suitable for re-implantation.

While cell and gene therapies are expected to expand rapidly in the coming years, a remaining key challenge for researchers and producers is assessing these complicated, living medicines during manufacturing. As developed by NIRRIN Bioprocess Analytics, Inc., Billerica, Mass., the use of NIR laser technology, which has the ability to precisely measure cell growth rates and quantify key metabolites in cell cultures, offers a highly useful mechanism for achieving this goal. Techniques described above as well as other NIR approaches can be integrated into complex cell and gene therapy production processes, providing valuable insight into cellular behavior and phenotypes. An illustration is presented through FIG. 18, which compares samples of *Pichia* being grown in a shake flask and studied using MR measurements performed with an in-line probe taking samples automatically and reading absorbance at approximately 1450 nm with off-line measurements from a standard spectrophotometer.

In a specific example, aspect of the invention can be applied to the production of chimeric antigen receptor T (CAR-T) cells. This process begins with the collection and purification of a patient's own lymphocytes, which are then genetically engineered to target specific cell surface markers and expanded to create a therapeutic infusion product. Analysis of cell growth and density is critical to this process, as the U.S. Food and Drug Administration (FDA) requires each CAR-T batch to contain a minimum number of cells. In addition, assessment of cellular phenotype via measurement of secreted metabolites, cytokines, and/or other factors can offer insight into the manufacturing process. Applying techniques described herein, this information can be obtained without the need for manual sampling, increasing efficiency and reducing the risk of contamination. In addition to CAR-T therapies, applications can also target the production of allogeneic CAR-T cells, tumor infiltrating lymphocyte therapies, induced pluripotent stem cell treatments, and other ex vivo cell or gene therapy product.

In sum, procedures and techniques relying on NIR laser technology have the potential to enter the cell and gene therapy production process and provide important insight into cell quality and therapy development. From determining cell number and density to precisely measuring secreted factors of interest, there are a number of valuable uses for biomanufacturers working on next generation therapies.

While this invention has been particularly shown and described with references to preferred embodiments thereof, it will be understood by those skilled in the art that various changes in form and details may be made therein without departing from the scope of the invention encompassed by the appended claims.

What is claimed is:

1. A device for monitoring a vessel, the device comprising:
    an outer tube;
    a tunable laser that sweeps a narrow band light emission across an infrared spectral band, wherein the light emission from the tunable laser is generated outside the vessel; and
    a tip section at the end of the tube, the tip section having a sample detection region defined by an optical transmission port, through which the light emission from the tunable laser passes, and an optical detection port, wherein the light emission received through the optical detection port is detected by a photodetector housed in the tip section with a controller resolving an absorption spectra of a sample in the sample detection region by monitoring spectral scanning of the tunable laser over its scan band relative to a time-response of the photodetector; and
    an inner tube housed in the outer tube for providing the light for the optical transmission port, wherein the inner tube defines a free space path for the light emission from the tunable laser to the optical transmission port.

2. The device as claimed in claim 1, wherein the inner tube contains electrical wiring for the photodetector.

3. The device as claimed in claim 1, wherein the inner tube contains optical fiber for carrying the light emission from the tunable laser for the optical transmission port.

4. The device as claimed in claim 1, further comprising a housing carried by the inner tube for making electrical connections to the optical detector.

5. The device as claimed in claim 1, further comprising a fitting on the outer tube for sealing with a port of a bioreactor.

6. The device as claimed in claim 1, further comprising a focusing lens in the tip section for conditioning the light emission transmitted across the sample detection region.

7. The device as claimed in claim 1,
    wherein the light emission from the tunable laser is from 780 to 2500 nm.

8. A method for monitoring a vessel, the method comprising:
    inserting an outer tube with a tip section into the vessel;

sweeping a narrow band light emission from a tunable laser across an infrared spectral band, wherein the light emission from the tunable laser is generated outside the vessel;

transmitting the light emission from the tunable laser and across a sample detection region of the tip section from an optical transmission port to an optical detection port, wherein an inner tube is housed in the outer tube and provides the light for the optical transmission port, wherein the inner tube defines a free space path for the light emission from the tunable laser to the optical transmission port;

detecting the light emission received through the optical detection port with a photodetector housed in the tip section; and resolving an absorption spectra of a sample in the sample detection region by monitoring spectral scanning of the tunable laser over its scan band relative to a time-response of the photodetector.

9. The method of claim 8, further comprising autoclaving the outer tube including the tip section prior to inserting the outer tube into the vessel.

10. The method of claim 8, further comprising, after inserting the outer tube into the vessel, inserting an inner tube including a housing into the outer tube.

11. The method of claim 8, wherein the sample detection region is defined by a lens and the photodetector.

12. The method of claim 8, wherein the light emission from the tunable laser is from 780 to 2500 nm.

13. The method of claim 8, further comprising transmitting the light emission from the tunable laser to the vessel.

14. The method of claim 8, further comprising directing the light emission from the tunable laser towards the tip section through one or more of a fiber, a collimator and a free space path.

15. A system comprising:
a bioreactor; and
a device for monitoring in-situ contents in the bioreactor, wherein the device includes:
an outer tube inserted through a port of the bioreactor;
a tunable laser that sweeps a narrow band light emission across an infrared spectral band, wherein the light emission from the tunable laser is generated outside the bioreactor;
a tip section at the end of the tube, the tip section having a sample detection region defined by an optical transmission port, through which the light emission from the tunable laser passes, and an optical detection port, wherein the light emission received through the optical detection port is detected by a photodetector housed in the tip section with a controller resolving an absorption spectra of a sample in the sample detection region by monitoring spectral scanning of the tunable laser over its scan band relative to a time-response of the photodetector; and
an inner tube housed in the outer tube for providing the light for the optical transmission port, wherein the inner tube defines a free space path for the light emission from the tunable laser to the optical transmission port.

16. A system as claimed in claim 15, wherein the bioreactor is a stir tank or a rocking bioreactor.

17. A device for monitoring a vessel, the device comprising:
an outer tube;
a tunable laser that sweeps a narrow band light emission across an infrared spectral band;
a tip section at the end of the tube, the tip section having a sample detection region defined by an optical transmission port, through which the light emission from the tunable laser passes, and an optical detection port, wherein the light emission received through the optical detection port is detected by a photodetector housed in the tip section with a controller resolving an absorption spectra of a sample in the sample detection region by monitoring spectral scanning of the tunable laser over its scan band relative to a time-response of the photodetector; and
an inner tube housed in the outer tube for providing the light for the optical transmission port, wherein the inner tube defines a free space path for the light emission from the tunable laser to the optical transmission port.

* * * * *